(12) United States Patent
Weidner et al.

(10) Patent No.: US 11,357,654 B2
(45) Date of Patent: Jun. 14, 2022

(54) SYSTEM AND METHOD FOR REDUCING FORCES ACTING ON A SPINAL COLUMN

(71) Applicant: EXOIQ GmbH, Hamburg (DE)

(72) Inventors: Robert Weidner, Hamburg (DE); Tabias Meyer, Hamburg (DE); Jens Peter Wulfsberger, Hamburg (DE)

(73) Assignee: EXOIQ GmbH, Hamburg (DE)

( * ) Notice: Subject to any disclaimer, the term of this patent is extended or adjusted under 35 U.S.C. 154(b) by 417 days.

(21) Appl. No.: 16/461,238

(22) PCT Filed: Nov. 14, 2017

(86) PCT No.: PCT/DE2017/100966
§ 371 (c)(1),
(2) Date: May 15, 2019

(87) PCT Pub. No.: WO2018/091037
PCT Pub. Date: May 24, 2018

(65) Prior Publication Data
US 2019/0274862 A1 Sep. 12, 2019

(30) Foreign Application Priority Data
Nov. 18, 2016 (DE) .................. 10 2016 122 282.8

(51) Int. Cl.
*A61F 5/02* (2006.01)
*B25J 9/00* (2006.01)
(52) U.S. Cl.
CPC ............... *A61F 5/026* (2013.01); *A61F 5/02* (2013.01); *A61F 5/022* (2013.01); *B25J 9/0006* (2013.01)

(58) Field of Classification Search
CPC .. A61F 5/026; A61F 5/02; A61F 5/022; A61F 5/01; A61F 5/0102; A61F 5/0125;
(Continued)

(56) References Cited

U.S. PATENT DOCUMENTS 3,358,678 A  12/1967  Kultsar
3,467,421 A   9/1969  Bentley
(Continued)

FOREIGN PATENT DOCUMENTS

CN  104552276 A  4/2015
CN  104552276 B  2/2016
(Continued)

OTHER PUBLICATIONS

International Search Report dated Apr. 12, 2018, issued in PCT Application No. PCT/DE2017/100966, filed Nov. 14, 2017.

*Primary Examiner* — Ophelia A Hawthorne
(74) *Attorney, Agent, or Firm* — Workman Nydegger

(57) ABSTRACT

A system for reducing forces which, in particular, act on a spine of a human, includes a plurality of joinable exoskeleton elements, wherein at least two of the joinable exoskeleton elements are configured to be fastened to the human body during use of the system and wherein a first exoskeleton element of the joinable exoskeleton elements includes a guide which is configured to guide a second exoskeleton element of the joinable exoskeleton elements along a curved trajectory relative to the first exoskeleton element and to enforce a superimposed translational and rotational relative movement between the first exoskeleton element and the second exoskeleton element when guiding the second exoskeleton element along the curved trajectory relative to the first exoskeleton element.

19 Claims, 4 Drawing Sheets

(58) Field of Classification Search
CPC .. A61F 5/0193; A61F 5/05; A61F 5/37; A61F 13/048; A61F 2007/003; A61F 5/05883; A61F 5/3715; A61F 5/028; A61F 5/058; A61F 13/12; A61F 2007/0024; B25J 9/0006

See application file for complete search history.

(56) References Cited

U.S. PATENT DOCUMENTS

| | | | |
|---|---|---|---|
| 5,259,833 A * | 11/1993 | Barnett | A61F 5/026 2/44 |
| 5,282,460 A | 2/1994 | Boldt | |
| 5,328,447 A * | 7/1994 | Kapounek | A41D 13/0531 128/846 |
| 5,865,770 A | 2/1999 | Schectman | |
| 6,113,642 A | 9/2000 | Petrofsky et al. | |
| 2003/0004473 A1 | 1/2003 | Bonadio et al. | |
| 2003/0223844 A1 | 12/2003 | Schiele et al. | |
| 2007/0258671 A1 | 11/2007 | Siemer et al. | |
| 2008/0009771 A1 | 1/2008 | Perry et al. | |
| 2008/0188907 A1 | 8/2008 | Aguirre-Ollinger et al. | |
| 2010/0041521 A1 | 2/2010 | Ingvast et al. | |
| 2011/0004322 A1 | 1/2011 | Sankai | |
| 2012/0172770 A1 | 7/2012 | Almesfer et al. | |
| 2014/0212243 A1 | 7/2014 | Yagi et al. | |
| 2015/0266181 A1 | 9/2015 | Kornbluh et al. | |
| 2015/0366694 A1 | 12/2015 | Bujold et al. | |
| 2016/0058647 A1 | 3/2016 | Maddry | |
| 2016/0067061 A1 | 3/2016 | Nagarajan et al. | |
| 2016/0325428 A1 | 11/2016 | Chun | |
| 2017/0259427 A1 | 9/2017 | Asada et al. | |

FOREIGN PATENT DOCUMENTS

| | | |
|---|---|---|
| CN | 105415353 A | 3/2016 |
| CN | 106313012 A | 1/2017 |
| CN | 106335049 A | 1/2017 |
| CN | 106945017 A | 7/2017 |
| CN | 206588942 U | 10/2017 |
| CN | 105415353 B | 1/2018 |
| CN | 106313012 B | 5/2018 |
| CN | 106335049 B | 8/2018 |
| DE | 307250 C1 | 9/1917 |
| DE | 10 2011 076843 A1 | 12/2012 |
| DE | 102011076843 B4 | 5/2014 |
| EP | 1364755 A1 | 11/2003 |
| EP | 1364755 B1 | 11/2009 |
| EP | 2796114 A1 | 10/2014 |
| EP | 2796114 B1 | 3/2016 |
| EP | 3189945 A1 | 7/2017 |
| EP | 3189945 B1 | 9/2018 |
| ES | 2544890 A1 | 9/2015 |
| FR | 779284 A | 4/1935 |
| FR | 2993811 A1 | 7/2012 |
| FR | 3046110 A1 | 12/2015 |
| JP | 03-665879 B2 | 4/2005 |
| JP | 2012024557 A | 2/2012 |
| JP | 2012239818 A | 12/2012 |
| KR | 10-2012-065470 A | 6/2012 |
| WO | 2005/105004 A1 | 11/2005 |
| WO | 2010/019300 A1 | 2/2010 |
| WO | 2010/019300 A9 | 2/2010 |
| WO | 2010/080774 A2 | 7/2010 |
| WO | 2011/127421 A1 | 10/2011 |
| WO | 2012/099995 A2 | 7/2012 |
| WO | 2012/099995 A3 | 8/2012 |
| WO | 2014/093408 A2 | 6/2014 |
| WO | 2014/093408 A3 | 9/2014 |
| WO | 2014/195373 A1 | 12/2014 |
| WO | 2015/078981 A1 | 6/2015 |
| WO | 2015/157473 A2 | 10/2015 |
| WO | 2016/012480 A1 | 1/2016 |
| WO | 2016/015070 A1 | 2/2016 |
| WO | 2016/146960 A1 | 9/2016 |
| WO | 2016/174091 A1 | 11/2016 |
| WO | 2016/187275 A1 | 11/2016 |
| WO | 2017/109190 A1 | 6/2017 |
| WO | 2017/109193 A1 | 6/2017 |
| WO | 2017/109196 A1 | 6/2017 |
| WO | 2017/109197 A1 | 6/2017 |
| WO | 2017/109202 A1 | 6/2017 |
| WO | 2017/167349 A1 | 10/2017 |

* cited by examiner

SYSTEM AND METHOD FOR REDUCING FORCES ACTING ON A SPINAL COLUMN

FIELD

The present invention relates to a wearable, modular, (exoskeletal) system which may, for example, be carried on the back of a human parallel to the spine to reduce stress on the spine/spinal musculature during ergonomically unfavorable activities such as, for example, load handling processes, or to support movements of people with musculoskeletal disorders, or to limit movements of people with musculoskeletal disorders to a specific range. In particular, the system enables redirecting forces to relieve the spine/spinal musculature.

BACKGROUND

Numerous technical systems are known in the art that support human movements in order to, for instance, improve the quality of manual working steps, the ergonomics of a workplace or the mobility of persons with musculoskeletal disorders. The systems address the whole body or individual parts of the body, such as, for example, the lower extremities, the upper extremities or the back.

Examples of actuated (active) systems are the Hybrid Assistive Limb (HAL), the ReWalk, the Boston Dynamics exoskeleton, or the Lucy support system, which can be used to support overhead work. All these systems have in common that they support the movement of the lower and/or upper extremities. An example of non-actuated (passive) systems are orthoses, such as spinal orthoses for stabilizing the spine in case of vertebral injuries. Orthoses are often based on rigid or semi-rigid back structures which specifically limit the freedom of movement.

Thus, while active and passive systems are known for a variety of use cases, there remains room for improvement in regard to enabling movements that are as natural as possible.

SUMMARY OF THE INVENTION

It is the object of the present invention to improve the systems known in the art.

This object is achieved by a system according to the invention. The system according to the invention comprises a plurality of joinable exoskeleton elements, wherein at least two of the joinable exoskeleton elements are adapted to be fastened to the human body during use of the system, and a first exoskeleton element of the joinable exoskeleton elements comprises a guide configured to guide a second exoskeleton element of the joinable exoskeleton elements along a curved trajectory relative to the first exoskeleton element and to enforce a superimposed translational and rotational relative movement between the first exoskeleton element and the second exoskeleton element when guiding the second exoskeleton element along the curved trajectory relative to the first exoskeleton element.

The joinable exoskeleton elements can thus be displaced relative to each other, wherein the distance and the orientation of the exoskeleton elements relative to each other change (within predetermined limits) during the displacement, i.e., different distances correlate with different orientations. For instance, at a first distance, a first orientation and at a second distance, a second orientation may be enforced or at least enabled whereas the second orientation is disabled at the first distance and the first orientation is disabled at the second distance.

In this context, the term "joinable" as used throughout the description and the claims particularly refers to a configuration enabling a (detachable) serial connection or chain. Further, the term "exoskeleton element" as used throughout the description and the claims particularly refers to a component which, in use of the system, contributes to realizing a support, hold, or force transmission function with respect to the human body.

Furthermore, the term "fastened" as used throughout the description and the claims particularly refers to a contacting in which forces acting on the spinal column can be redirected, as, for instance, the system rests or (partially) encloses or embraces the shoulder/chest area and the hip/pubic area. In addition, the term "trajectory" as used throughout the description and the claims particularly refers to a continuous path.

Preferably, the system further comprises an actuator unit, wherein the actuator unit is configured to controllably displace the second exoskeleton element relative to the first exoskeleton element.

Preferably, the centrode of the second exoskeleton element does not intersect with the first and second exoskeleton elements when guiding the second exoskeleton element along the curved trajectory relative to the first exoskeleton element.

Preferably, the centrode of the second exoskeleton element is offset relative to the first and second exoskeleton elements towards the spine when guiding the second exoskeleton element along the curved trajectory relative to the first exoskeleton element.

Preferably, the centrode of the second exoskeleton element matches or coincides with the centrode of a vertebra or a group of vertebrae of the spine, when guiding the second exoskeleton element along the curved trajectory relative to the first exoskeleton element.

Preferably, a first guide member of the second exoskeleton element is slidably mountable to the guide, wherein the second exoskeleton element is guided along the curved trajectory relative to the first exoskeleton element when sliding the first guide member along the guide.

By suitably shaping the trajectory, a deviation between the movement of the instant center of rotation of the vertebrae of the human spine and the movement of the instant center of rotation of the corresponding exoskeleton elements can be (essentially) reduced to zero and thus, no or only negligible relative movements occur between the connection points of the system and the human body and the human body when flexing or extending the spine.

Preferably, the second exoskeleton element has a base member and the first guide member of the second exoskeleton element is rotatably supported relative to the base member, wherein rotation of the first guide member of the second exoskeleton element relative to the base member enables guiding the second exoskeleton element relative to the first exoskeleton element along a second curved trajectory.

This allows for more complex movements in addition to flexing and extending the spine such as, for example, lateral bending or twisting the spine around the vertical axis.

Preferably, a second guide member of the second exoskeleton element is slidably mountable to the guide, wherein the first guide member and the second guide member are spaced from each other along a straight line.

This can increase the stability of the movement and reduce the wear of the system.

Preferably, during use of the system, the straight line is in a plane defined by a portion of the curved trajectory.

By guiding the guide members by means of two separate guide elements, which are guided along different guide paths or different sections of a guide path, it is possible to achieve arbitrarily complex correlations between distance and alignment in addition to, for example, circular trajectories.

Preferably, a distance between the first guide member and the second guide member or a center of gravity of the second exoskeleton element is continuously adjustable or adjustable in steps, wherein different distances result in differently curved trajectories.

Due to the adjustability of the curvature of the trajectory, a deviation between a motion of the instant center of rotation of the vertebrae of the spine of the human and a motion of the instant center of rotation of corresponding exoskeleton elements can be (substantially) reduced to zero, without customized exoskeleton elements.

Preferably, the guide is continuously adjustable or adjustable in steps, wherein different adjustments result in differently curved trajectories.

As already stated, the adjustability of the curvature of the trajectory allows reducing a deviation between a motion of the instant center of rotation of the vertebrae of the spine of the human and a motion of the instant center of rotation of corresponding exoskeleton elements (substantially) to zero, without customized exoskeleton elements being required.

Preferably, the first exoskeleton element and the second exoskeleton element are provided with first receptacles, wherein the first receptacles are adapted to receive a first actuator unit for controllably displacing the second exoskeleton element along the curved trajectory relative to the first exoskeleton element.

This allows actively supporting a movement of the person, for example, the flexing and extending of the spine or the upper body.

Preferably, the first exoskeleton element and the second exoskeleton element are provided with second receptacles which are adapted to receive a second actuator unit for controllably displacing the second exoskeleton element along the curved trajectory relative to the first exoskeleton element, wherein the first receptacles and the second receptacles are offset from a plane defined by the curved trajectory.

Thereby, a torque around an axis perpendicular to the guide direction can be generated, which can be used to actively support lateral bending or twisting the spine around the vertical axis.

Preferably, the first exoskeleton element and/or the second exoskeleton element are provided with a sensor unit for determining a distance or an angle between the first exoskeleton element and the second exoskeleton element.

This allows for a more precise control of the motion support.

Preferably, a method for reducing forces which act on a spine of a human during motion comprises joining the exoskeleton elements of the system, fastening the system to a body of the human, determining a deliberate extending or flexing of the spine of the human and, in response to the determining, displacing the second exoskeleton element along the curved trajectory relative to the first exoskeleton element.

This allows supporting a deliberate extending or flexing of the spine of the human and reducing the load of the spine or the spinal musculature as, for instance, the forces otherwise acting on the upper portion of the spine are absorbed and redirected by the system.

Preferably, the determining of the deliberate extending or flexing of the spine of the human comprises utilizing human-mounted sensors of a sensor unit.

This allows for more rapidly and accurately detecting a deliberate extending or flexing of the spine.

Preferably, the method further comprises adjusting the curved trajectory to a movement pattern of the human when extending or flexing the spine.

Due to the adjusting, a movement of the exoskeleton elements can be adapted even more accurately to the movement of a spine.

Preferably, the adjusting comprises reducing deviations between a motion of the instant center of rotation of the vertebrae of the spine of the human and a motion of the instant center of rotation of corresponding exoskeleton elements.

As a result, a support of the spine and the spinal musculature can be achieved which largely follows the natural course of motion.

BRIEF DESCRIPTION OF DRAWINGS

The invention will be explained in more detail in the detailed description on the basis of exemplary embodiments, wherein reference is made to the drawings in which.

In the drawings, the same and functionally similar elements are indicated by the same reference numerals.

DESCRIPTION OF THE EMBODIMENTS

Figure 1:
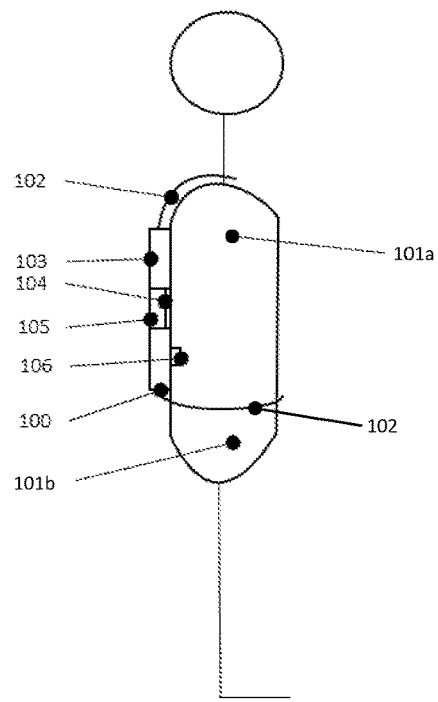
FIG. 1 shows an example of an arrangement of a system according to the invention on a human body in a schematic body side view.

FIG. 1 shows a wearable system 100 comprising two exo-vertebrae 103 arranged parallel to the spine of a human. The system 100 is connected to the upper body 101*a* (e.g., to the shoulders) and to the lower body 101*b* (e.g., to the lower back/pelvis) of the human via connectors 102. As shown in FIG. 1, the connectors 102 may (partially) enclose or span the shoulders or pelvis and/or be integrated into (textile) garments which allow force to be transmitted between the system 100 and the user's body. Further, each exo-vertebra 103 may abut on the back, i.e., be in contact with the back of the user during use (possibly indirectly via a (textile) garment in which the system 100 is integrated).

Figure 2:
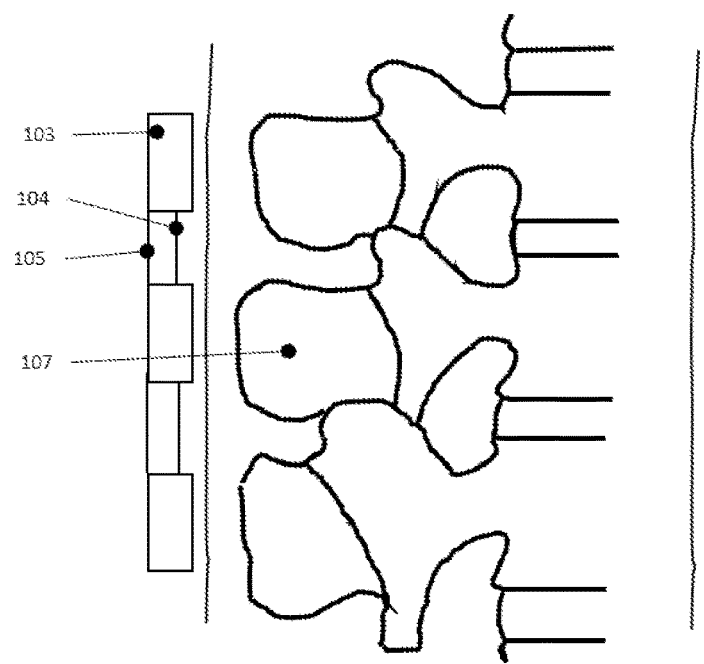
FIG. 2 shows an example of an arrangement of exoskeleton elements (exo-vertebrae) of a system according to the invention in relation to a human spine in a schematic body side view.

As shown in FIG. 1 and FIG. 2, an exo-vertebra 103 may correspond to or span several or a single human vertebra. Alternatively, several exo-vertebrae 103 may correspond to or span one human vertebra. In particular, an exo-vertebra 103 may correspond to or span one or an integral number of human vertebrae. Further, as shown in FIG. 2, exo-vertebrae 103 and human vertebrae may be horizontally juxtaposed when the spine is extended, wherein an (imaginary) horizontal line through an exo-vertebra 103 also extends through a center of gravity of a human vertebra.

As shown in FIG. 1 and FIG. 2, two joined exo-vertebrae 103 are connected to each other via a guide member 104, wherein the lowermost and the uppermost exo-vertebra 103 (i.e., the terminal exo-vertebrae 103) are connected on the respective outer side to the user 101 through connectors 102. The exo-vertebrae 103 are, as described in more detail below with reference to FIG. 3-FIG. 6, configured to allow a rotational-linear relative movement. By this, the relative movement of the exo-vertebrae 103 to each other can be designed in a way that their instant center of rotation at least approximately coincides with the pivot point of the corresponding human vertebrae.

In addition, an actuator unit 105 may be provided between each two exo-vertebrae 103. The actuator unit 105 can be used to (actively) displace the exo-vertebrae 103 relative to one another and to thereby accelerate a human movement or (possibly depending on the direction) to decelerate it (or to support it). The actuator units 105 may, for example, be provided with electric motors, artificial muscles, pneumatic or hydraulic actuators, mechanical springs and shape memory alloys. The actuator units 105 may also be connected to a power source, for example an accumulator, or a fluid source, which supplies the actuator units 105 with electrical energy or a (pressurized) fluid.

The system 100 may further include a control unit (not shown) that controls the system 100, and in particular the actuator units 105, and, optionally, enables operation of the system 100 in various control modes. For example, a control mode may provide for the actuator units 105 to be freewheeled within a particular range in which human movements can be made freely, or not much supported, and to prevent, slow down, or assist movements outside of the particular range. Another control mode may, for example, provide that the actuator units 105 support any movements of the human or movements for which support is manually requested ("at the touch of a button"). Yet another control mode may, for example, evaluate load data, which, for example, may be measured by sensors of a sensor unit 106, wherein the support level is adjusted based on the load data. For instance, electromyographic (EMG) or force sensors may be used to control the system 100 based on the load. For example, at low loads, the system 100 may initially be inactive and only become active when the load exceeds a critical value.

Figure 3:
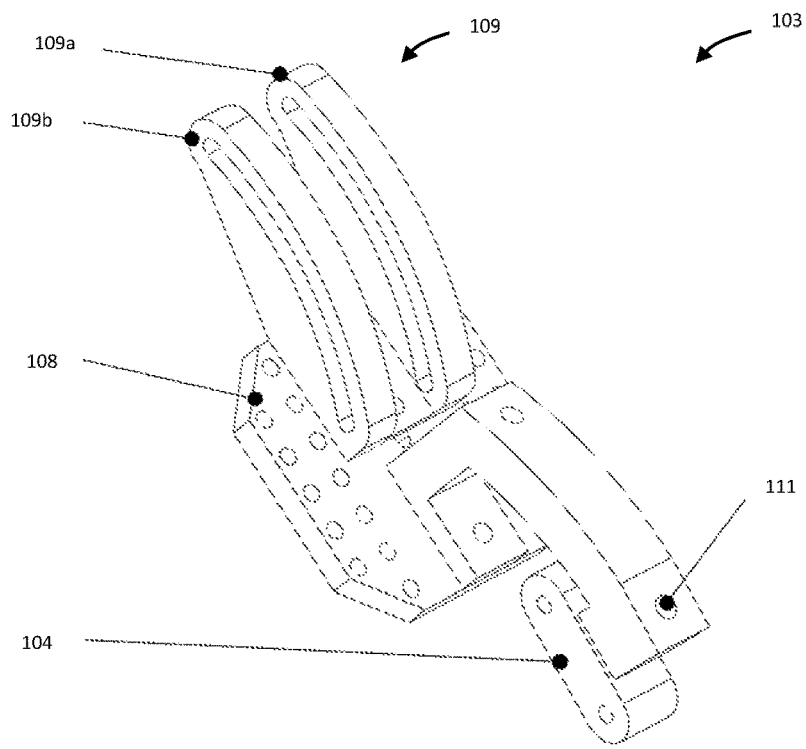
FIG. 3 shows an example of an embodiment of an exo-vertebra in oblique side view.

FIG. 3 shows an exemplary exo-vertebra 103. The exo-vertebra 103 shown in FIG. 3 comprises a base member 108 (shown here in the form of a flat plate) which has a guide 109 on a first (vertical) connecting side and a guide member 110 on a second (opposite) connecting side. The guide 109 comprises two parallel guide plates 109a and 109b with arcuate recesses. In use, the exo-vertebrae 103 may be arranged relative to the spine in such a way that the center of the arc on which two adjacent exo-vertebrae 103 move (i.e., the instant center of rotation of the exo-vertebrae 103) is congruent with the rotational center (for an instant center of rotation which is assumed to be substantially fixed) of the corresponding underlying human vertebrae. Due to this mechanical behavior, the exoskeletal structure undergoes an elongation in the case of a ventral flexion of the user's back, that corresponds to the elongation of the user's back, which causes that the exo-vertebrae 103 can be fixedly arranged on the back.

Figure 4:
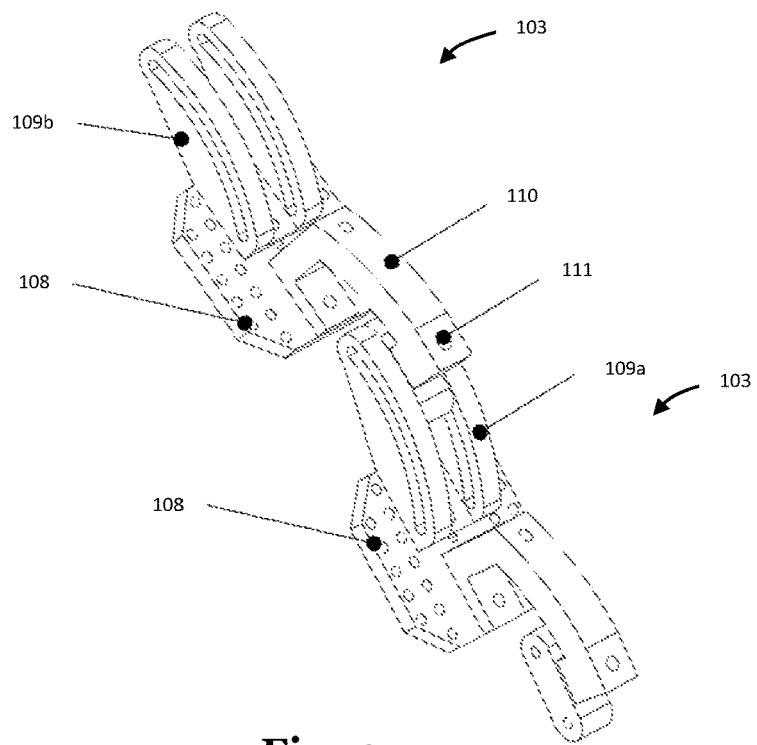
FIG. 4 shows an example of two joined exo-vertebrae according to FIG. 3 in an oblique side view.

The guide member 104, which is formed in FIG. 3 and FIG. 4 as a carriage of a cantilever 110, comprises two recesses for receiving guide pins, which, as shown in FIG. 4, realize a sliding bearing of the guide member 104 in the guide 109 of the joined exo-vertebra 103 when sliding in the arcuate recesses. The guide member 104 is further connected to the base member 108 via a pivot bearing 111. Due to the pivot bearing 111, which is located in the plane of rotation of the first connection and has an axis of rotation (which is preferably directed at the instant center of rotation), a rotational degree of freedom can be added to the chain of exo-vertebrae 103. In addition to flexing and extending of the exo-vertebral column formed by the exo-vertebrae 103, the further degree of freedom enables oblique flexing and extending, too.

The base member 108 of the exo-vertebra 103 is further provided with connection means in the form of a hole grid which allows making a connection to a connector 102. Furthermore, the actuator units 105 may be attached to the hole grid, for example, on both sides of the cantilever 110. Furthermore, an actuator unit 105 may be attached to two consecutive exo-vertebrae 103 or to more than two exo-vertebrae 103 which are displaced relative to each other by, for example, an electric motor and a cable pull at a same transmission ratio or at different transmission ratios. Thus, for example, an actuator unit 105 may displace adjacent exo-vertebrae 103 in the direction of the actuator unit 105 by means of a cable pull which extends to the adjacent exo-vertebrae 103.

Figure 5:
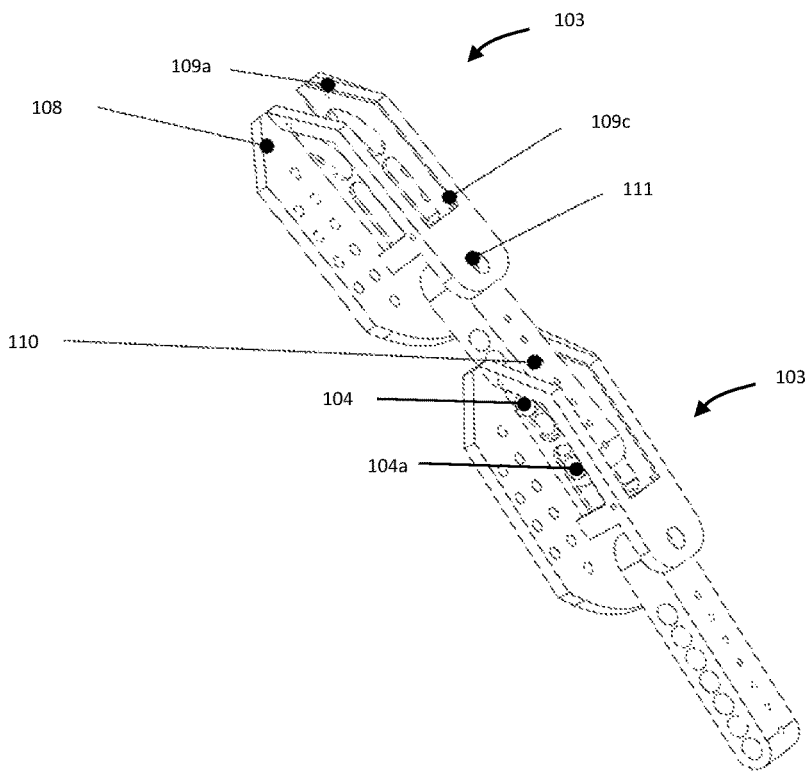
FIG. 5 shows an example of two joined exo-vertebrae in an oblique side view, according to a further embodiment.
Figure 6:
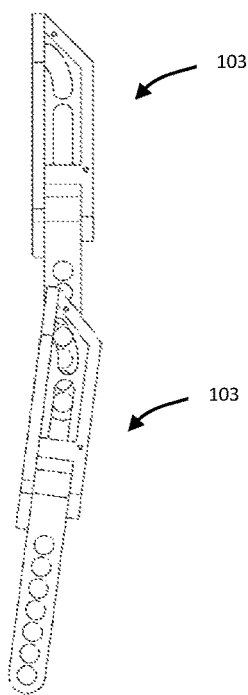
FIG. 6 shows a side view of the joined exo-vertebrae of FIG. 5 in extended position.

FIG. 5 and FIG. 6 show another example of two joined exo-vertebrae 103. The exo-vertebrae 103 shown in FIG. 5 and FIG. 6 differ from the exo-vertebrae 103 shown in FIG. 3 and FIG. 4 in that instead of one arcuate recess, there are two recesses (guideways) per plate 109a and 109b, wherein a first guide member 104, which is formed by a first pin that is insertable into a recess of the cantilever 110, is slidably mounted to the first guideway of the first plate 109a, and a second guide member 104a which is offset in the track direction and is formed by a second pin that is insertable into a recess of the cantilever 110, is slidably mounted to a second guideway 109c of the first plate 109a. The provision of a plurality of guideways and associated guide pins causes a rotation characteristic with a moving instant center of rotation. In order to be able to subsequently adapt the motion of the instant center of rotation, the guide plates 109a and 109b are made exchangeable, so that plates with different guideway courses can be used. As complex centrodes can be realized with the described guiding technique, it is also possible to span a large number of vertebrae 103 with only one exo-vertebra 103.

As shown in FIG. 5 and FIG. 6, the cantilever 110 further comprises a series of recesses, so that both, the distance of the insertable pins relative to each other as well as to the center of gravity of the respective exo-vertebra 103 is adjustable. It is understood that as an alternative to the series of recesses, a continuous mechanism for adjusting the distance between the insertable pins to each other or the center of gravity of the respective exo-vertebra 103 may be realized, for example, by means of a continuous recess in which the pins can be clamped at any position.

The systems 100 shown in FIG. 1 to FIG. 6 serve to support the spine/spinal musculature. The exoskeletal structure that can be formed by the shown exo-vertebrae 103 consists of several identical exo-vertebrae 103 connected in series, which are arranged along the spine and slidably connected to each other. By appropriate design or adaptation of the trajectories of the relative movement, the exo-vertebrae 103 can be arranged stationary on the back, since their distance from one another changes during the flexion or extension of the back.

Thus, since the overall structure does not experience tension when flexing the spine, a support can be achieved that does not or only minimally restrict natural movements, where the system 100 avoids a friction-prone movement relative to the body. Further, the exo-vertebrae 103 may be connected and guided against each other such that, when flexing the spine, they have a relative pivot point with respect to each other which is congruent with the effective pivot point of the underlying (human) vertebrae. In this way, the exoskeletal structure is able to follow the movement of the human spine, although it is offset from the bending line of the spine.

By means of actuator units 105 between the exo-vertebrae 103, pull- and/or push-forces and hence torques can be generated between the exo-vertebrae 103. Thus, when the exoskeletal structure is connected to the user's body via suitable connectors, the forces generated in the exoskeletal structure are transferred to the wearer's torso, thereby relieving the spine and spinal musculature. Hence, body movements in which the back is flexed and extended can be supported.

The system 100 may also be adapted to individual body characteristics of a user (especially anthropometry and movement characteristics) by adjustable exo-vertebrae 103 (as described in connection with FIG. 5 and FIG. 6). In particular, distance changes between the exo-vertebrae 103 can be set into a desired relationship with the change in angle between the exo-vertebrae 103 by means of adjustably configured exo-vertebrae 103. Thus, the system 100 can be individually adapted to the anatomy of the user, thereby enabling optimal support behavior. Further, the system 100 is scalable in length by adding or omitting exo-vertebrae 103 or by using exo-vertebrae 103 of different dimensions. In addition, the rigidity/softness/elasticity of the exo-vertebrae 103 can be adjusted via the geometric shape and the materials used.

Overall, a system 100 of low complexity is provided, where the geometric shape and the materials can be used to adjust the motion characteristics and only linear motion actuations are required. In addition, a system 100 is provided which has a high number of identical parts. The system 100 further enables the realization of a defined relationship of relative rotation to translation during human motions through predetermined real-world trajectories of the exo-vertebrae 103 relative to one another.

The system 100 may, as stated above, be used to support people who have to perform tasks which are ergonomically unfavorable or repetitive or last over a long period of time, or who suffer from impairments, e.g., due to a back injury. In addition, the use for stabilizing at least parts of elastic or flexible technical elements or technical joints or the support of other living beings is possible. As a result, at least a part of a body of a person or of another living being or of a technical system (such as an industrial robot) can be relieved or spared by a force redirection and amplification, which enables the execution of certain activities in the first place.

Figure 7:
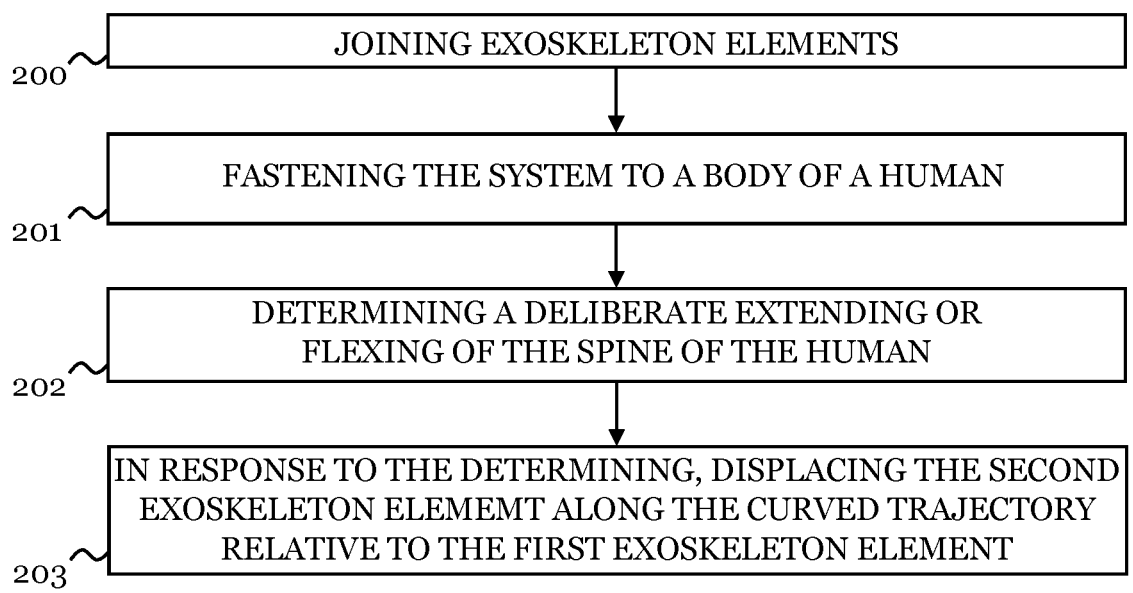
FIG. 7 shows a method for reducing forces acting on a spine of a human during motion.

In this regard, FIG. 7 shows a method of using the system 100. After analyzing the kinematic conditions, matching exo-vertebrae 103 are selected from a variety of different exo-vertebrae 103 (such as exo-vertebrae 103 that differ in their dimensions and materials used) and provisioned. Thereafter, the exo-vertebrae 103 are joined as indicated in step 200 and fastened to the body of a human, another being or even a technical system in step 201. Optionally, when using adjustable exo-vertebrae 103 (as shown in FIG. 5 and FIG. 6), the system 100 may be adjusted to a body's motion characteristic as described above by, for example, reducing deviations between a motion of the instant center of rotation of the vertebrae of the human spine and the motion of the instant center of rotation of the exoskeleton elements 103 by adjusting the trajectory. If deliberate extending or flexing of the spine is detected by means of a sensor unit 206 (step 202), the actuator units 105 can be actuated in response to the determination in step 203, such that the exo-vertebrae 103 are displaced against each other and the exoskeletal structure formed by system 100 flexes or extends as a result thereof.

LIST OF REFERENCE NUMERALS

100 system
101*a* upper body
101*b* lower body
102 connector
103 exoskeleton element
104, 104*a* guide member
105 actuator unit
106 sensor unit
107 human vertebra
108 base member
109, 109*a* guide
109*b*, 109*c* guide
110 cantilever
111 pivot bearing

The invention claimed is:

1. A system for reducing forces acting on a spine of a human, the system comprising a plurality of joinable exo-vertebrae; wherein
   at least two of the joinable exo-vertebrae are configured to be fastened to the human body during use of the system;
   a first exo-vertebra of the joinable exo-vertebrae comprises a guide which is configured to guide a second exo-vertebra of the joinable exo-vertebrae along a curved trajectory relative to the first exo-vertebra and to enforce a superimposed translational and rotational relative movement between the first exo-vertebra and the second exo-vertebra when guiding the second exo-vertebra along the curved trajectory relative to the first exo-vertebra; and
   an actuator is configured to controllably displace the second exo-vertebra relative to the first exo-vertebra.

2. The system of claim 1, wherein a first guide member of the second exo-vertebra is slidably mountable to the guide, wherein the second exo-vertebra is guided along the curved trajectory relative to the first exo-vertebra when sliding the first guide member along the guide.

3. The system of claim 2, wherein a second guide member of the second exo-vertebra is slidably mountable to the guide, wherein the first guide member and the second guide member are spaced from each other along a straight line.

4. The system of claim 3, wherein, during use of the system, the straight line is in a plane defined by a portion of the curved trajectory.

5. The system of claim 4, wherein a distance between the first guide member and the second guide member or a center of gravity of the second exo-vertebra is continuously adjustable or adjustable in steps, wherein different distances result in differently curved trajectories.

6. A method for reducing forces acting, in particular, on a spine of a human, comprising:
   joining the exo-vertebrae of the system according to claim 1;
   fastening the system to a body of the human;

determining a deliberate extending or flexing of the spine of the human; and in response to the determining, displacing the second exo-vertebra along the curved trajectory relative to the first exo-vertebra.

7. The method of claim 6, further comprising adjusting the curved trajectory to a movement pattern of the human when extending or flexing the spine.

8. The method of claim 7, wherein the adjusting comprises reducing deviations between a motion of the instant center of rotation of the vertebrae of the spine of the human and a motion of the instant center of rotation of corresponding exo-vertebrae elements.

9. The method of claim 6, wherein the determining of the deliberate extending or flexing of the spine of the human comprises utilizing human-mounted sensors of a sensor unit.

10. The system of claim 1, wherein the first exo-vertebra and the second exo-vertebra are provided with first receptacles, the first receptacles being adapted to receive a first actuator for controllably displacing the second exo-vertebra along the curved trajectory relative to the first exo-vertebra.

11. The system of claim 10, wherein the first exo-vertebra and the second exo-vertebra are provided with second receptacles, the second receptacles being adapted to receive a second actuator for controllably displacing the second exo-vertebra along the curved trajectory relative to the first exo-vertebra, wherein the first receptacles and the second receptacles are offset from a plane defined by the curved trajectory.

12. The system of claim 11, wherein the first exo-vertebra and/or the second exo-vertebra are provided with a sensor for determining a distance or an angle between the first exo-vertebra and the second exo-vertebra.

13. The system of claim 1, wherein a centrode of the second exo-vertebra does not intersect with the first and second exo-vertebrae when guiding the second exo-vertebra along the curved trajectory relative to the first exo-vertebra.

14. The system of claim 1, wherein a centrode of the second exo-vertebra is offset relative to the first and second exo-vertebrae when guiding the second exo-vertebra along the curved trajectory relative to the first exo-vertebra.

15. The system of claim 1, wherein a centrode of the second exo-vertebra is configured to match or coincide with a centrode of a vertebra or a group of vertebrae of the spine, when guiding the second exo-vertebra along the curved trajectory relative to the first exo-vertebra.

16. The system of claim 1, wherein the second exo-vertebra has a base member and the first guide member of the second exo-vertebra is rotatably supported relative to the base member, wherein rotation of the first guide member of the second exo-vertebra relative to the base member enables guiding the second exo-vertebra relative to the first exo-vertebra along a second curved trajectory.

17. The system of claim 1, wherein the guide is continuously adjustable or adjustable in steps, wherein different adjustments result in differently curved trajectories.

18. A system for reducing forces acting on a spine of a human, the system comprising a plurality of joinable exo-vertebrae; wherein at least two of the joinable exo-vertebrae are configured to be fastened to the human body during use of the system;

a first exo-vertebra of the joinable exo-vertebrae comprises a guide which is configured to guide a second exo-vertebra of the joinable exo-vertebrae along a curved trajectory relative to the first exo-vertebra and to enforce a superimposed translational and rotational relative movement between the first exo-vertebra and the second exo-vertebra when guiding the second exo-vertebra along the curved trajectory relative to the first exo-vertebra; and a centrode of the second exo-vertebra does not intersect with the first and second exo-vertebrae when guiding the second exo-vertebra along the curved trajectory relative to the first exo-vertebra.

19. A system for reducing forces acting on a spine of a human, the system comprising a plurality of joinable exo-vertebrae; wherein at least two of the joinable exo-vertebrae are configured to be fastened to the human body during use of the system;

a first exo-vertebra of the joinable exo-vertebrae comprises a guide which is configured to guide a second exo-vertebra of the joinable exo-vertebrae along a curved trajectory relative to the first exo-vertebra and to enforce a superimposed translational and rotational relative movement between the first exo-vertebra and the second exo-vertebra when guiding the second exo-vertebra along the curved trajectory relative to the first exo-vertebra; and a centrode of the second exo-vertebra is configured to match or coincide with a centrode of a vertebra or a group of vertebrae of the spine, when guiding the second exo-vertebra along the curved trajectory relative to the first exo-vertebra.

* * * * *